United States Patent [19]

Gsell et al.

[11] Patent Number: 4,886,836

[45] Date of Patent: Dec. 12, 1989

[54] ACTIVATED MEDIUM WITH LOW NON-SPECIFIC PROTEIN ADSORPTION

[75] Inventors: Thomas C. Gsell, Glen Cove; Richard F. Salinaro, Hasting-on-Hudson; Peter J. Degen, Huntington, all of N.Y.

[73] Assignee: Pall Corporation, Glen Cove, N.Y.

[21] Appl. No.: 56,943

[22] Filed: Jun. 3, 1987

[51] Int. Cl.$^4$ .................................................. C08J 9/36
[52] U.S. Cl. ...................................... 521/53; 521/54; 521/55; 521/134; 521/139; 521/901; 521/905; 435/180; 435/181; 435/182; 436/531; 436/532; 436/548; 436/824; 436/825; 436/827; 436/828; 210/493.38; 210/502.1
[58] Field of Search ...................... 521/53, 54, 55, 134, 521/139, 901, 905; 435/180, 181, 182; 436/531, 532, 548, 824, 825, 827, 828; 210/493.38

[56] References Cited

U.S. PATENT DOCUMENTS

| 4,229,537 | 10/1980 | Hodgins et al. | 435/177 |
| 4,473,474 | 9/1984 | Ostreicher et al. | 210/636 |
| 4,490,290 | 12/1984 | Gani et al. | 530/413 |
| 4,549,011 | 10/1985 | Herzberg et al. | 536/31 |
| 4,560,504 | 12/1985 | Arnold | 530/389 |
| 4,615,985 | 10/1986 | Deutsch et al. | 436/531 |
| 4,618,533 | 10/1986 | Steuck | 428/315.7 |
| 4,693,985 | 9/1987 | Degen et al. | 436/531 |

FOREIGN PATENT DOCUMENTS

| 1391028 | 4/1975 | |
| 0047953 | 9/1981 | European Pat. Off. . |
| 0066165 | 5/1982 | European Pat. Off. . |
| 0221046 | 5/1987 | European Pat. Off. . |
| 2015553 | 9/1979 | United Kingdom . |
| 2140424 | 11/1984 | United Kingdom . |
| 2184732 | 7/1987 | United Kingdom . |

Primary Examiner—John Kight
Assistant Examiner—Samuel A. Acquah
Attorney, Agent, or Firm—Leydig, Voit & Mayer

[57] ABSTRACT

A porous chemically activated medium having a low affinity for peptide group-containing materials is provided comprising a porous polymeric medium having a low affinity for peptide group-containing materials covalently bound to a residue of an activating agent which is capable of reacting with an acceptor molecule.

65 Claims, No Drawings

ACTIVATED MEDIUM WITH LOW NON-SPECIFIC PROTEIN ADSORPTION

TECHNICAL FIELD

The present invention relates to materials used for and to methods of immobilizing compounds, typically of a proteinaceous nature, and to methods of using such materials. More particularly, the present invention is directed to a surface modified porous, polymeric medium having low non-specific protein affinity useful in the controlled covalent binding of biological and/or proteinaceous materials and to processes using these media, such as diagnostic testing and filtration/separation applications.

Background Art

In contrast to the often elaborate procedures and unwieldy, expensive equipment sometimes required in clinical diagnoses and for the separation of biological materials in the recent past, advances in medical research have led to the development both of simpler procedures and equipment. Whereas techniques employed previously involved multiple steps and, in some cases, required both a high degree of dexterity and familiarity with the procedures, kits and devices are now available which in some instances allow one with little or no laboratory experience to quickly and accurately perform diagnostic tests or separations. Many of the test techniques and devices provide a visible indication of a positive test, such as a color change, resulting from the reaction of (1) a substance being analyzed for (analyte) with (2) a detection reagent or series of reagents. The analyte and/or test reagent may be simple chemical substances or more complex macromolecular substances ften found in a biological specimen. The visible indication of the presence of the analyte may take place in solution, or on a solid surface, such as the interior surface of a glass or plastic tube, the well of a spot or a multiwell plate, or on a porous material such as a filter paper or membrane. Because of the typical white background of a porous material, a preference has existed for such materials in some instances and has also been incorporated in the form of porous membranes or matrices in test devices used alone or in specific test kits.

The test reagents used in the media employed in many of the clinical and diagnostic tests are typically covalently bound to the media in a controlled manner. When the test reagent is of a biological nature, it is frequently a proteinaceous material, such as an antibody or antigen, which has a unique affinity to a particular substance or class of substances. With such diagnostic media, the analyte, if present in the fluid being tested, forms a strong complex with the test reagent which is bound to the support, and is detected using a detection reagent which signifies the presence and amount of the analyte by an appropriate means such as a change in absorption or emission of light in a particular portion of the electromagnetic spectrum, by enzymatic means or with radioactive labels. In the ideal test only the analyte binds to the diagnostic medium. Other materials, including the detection reagents which are themselves often proteinaceous, do not bind to the medium. In the actual testing of biological specimens, that is, fluids found in nature, which contain a plurality of components, many of these components, particularly those of a proteinaceous nature, are adsorbed by the diagnostic medium itself. Thus, in addition to those substances (analytes) for which the bound test reagent exhibits a specific affinity, due to the formation of a biospecific complex as, for example, between an antibody and an antigen, the diagnostic medium to which the test reagent is covalently bound also adsorbs substances of a proteinaceous nature other than the analyte in a non-specific manner. Such adsorption causes high background signals in a test and tends to diminish the sensitivity required for many diagnostic tests. Thus, both in automated and manual clinical diagnostic tests, particularly where low levels of analyte are present, non-specific sorption of proteinaceous materials by the medium tends to interfere with the test being performed. Such non-specific adsorption of proteins other than the analyte, and especially of the detection reagent itself, can give a false signal, i.e., noise, often referred to as "background". This noise is characteristic of the diagnostic medium and is not related to the amount of analyte present in the specimen. In a valid test, the signal resulting from the analyte must be greater than and distinguishable from the background. The greater the signal with respect to the noise, the greater is the reliability of the test. The reliability of such a diagnostic test may thus be described in terms of its "signal-to-noise" ratio, i.e., the ratio of the signal due to the analyte to the background or noise. In order for the analyte signal to be reliably detected at very low analyte concentrations, the signal-to-noise ratio must be high. Depending upon the nature of the test being performed, the biological sample, and the conditions under which the test is being performed, such background adsorption may render the results of the test meaningless even when the analyte tested for is present in the sample.

In addition to high background signals, prior art supports have an additional drawback. In many diagnostic applications, it is necessary to pass the analyte-containing fluid through the diagnostic medium. When such applications involve passage of solutions containing proteinaceous materials, particularly in filtration processes, the pressure differentials across the media frequently increase during use because continued contact of such media with proteinaceous materials results in the pores of the membrane being plugged with non-specifically sorbed proteinaceous material. Thus, a membrane which in most respects may be quite suitable for the intended diagnostic or laboratory procedure may be of limited value or, in some instances, rendered useless by an undesirble non-specific adsorption of proteinaceous material.

A further drawback of some of the activated media employed in separation or analytical applications is the susceptibility of the activated sites to hydrolysis, which destroys their ability to react with and bind protein and, therefore, reduces test sensitivity. Many chemically activated diagnostic media tend to react with moisture which results in fewer active sites capable of undergoing a desirable reaction. This reduces the capacity of these media to covalently bind protein.

Disclosure of the Invention

The present invention is directed to porous, polymeric media, preferably in membrane form and microporous in nature. The media, which have a low affinity or tendency to adsorb peptide group-containing substances, such as proteinaceous substances, in a non-specific manner contain active sites which comprise at least one functional group capable of reaction in a controlled manner with an acceptor molecule. This chemically activated medium can react with and covalently bind suitable acceptor molecules, typically a protein of a biological nature, after which it may be used as a separation or filtration material in the separation of specific substances, as a medium for affinity chromatography, or as a diagnostic test medium. Thus, the porous, polymeric medium to which the acceptor molecule is covalently bound is capable of further reaction and formation of a biospecific complex with a ligand present in a solution to remove the ligand therefrom. The ligand may subsequently be liberated from the medium to provide the ligand in purified form. Alternatively, when used in conjunction with suitable detection reagents, a diagnostic test may be performed when the acceptor molecule is a test reagent and the ligand is an analyte. The chemically activated media of the present invention make it possible to prepare biologically activated media specific to biological substances such as antibodies or antigens found in bodily fluids such as blood, plasma, sera, urine, etc., thereby allowing separation, purification, and/or identification of such biological substances.

Both the chemically activated media and the unactivated media used to prepare the chemically activated media of the present invention have a low tendency to adsorb peptide group-containing substances, particularly proteinaceous materials, in a non-specific manner as measured by the "Immersion Protein Binding Assay", discussed in greater detail below. The porous, polymeric medium from which the chemically active media of the present invention are formed preferably include a porous, and preferably microporous, polymeric substrate and a surface-modifying polymeric material formed and covalently bonded to or coated on the surface of the porous polymeric substrate. The porous, polymeric medium provides a hydroxyl-rich surface which has a low tendency to adsorb or low affinity for peptide group-containing materials, such as proteinaceous materials.

The porous, polymeric substrate is preferably microporous and liquophilic and most preferably hydrophilic. The substrate typically has a high affinity or sorbability for peptide group-containing materials, particularly proteinaceous materials. The surface of the porous polymeric substrate is modified to provide a low affinity for peptide group-containing materials by incorporation thereat, either by (1) coating or by (2) grafting, preferably the latter, a second polymeric material which is rich in available hydroxyl groups.

The surface-modifying polymer which is in the first form, i.e., a coating on the porous polymeric substrate, is a cross-linked polymer resulting from the reaction, typically a condensation reaction, of (a) a polymer having a plurality of hydroxyl moieties with (b) a cross-linking agent having functional groups or moieties capable of reacting with the hydroxyl moieties on the polymer. Preferably, the cross-linking agent is also a polymer.

The porous polymeric medium of the present invention, which employs a polymer coating, may be prepared by contacting a porous polymeric substrate with a mixture of a polymer having a plurality of hydroxyl moieties and a cross-linking agent having moieties capable of undergoing a reaction, preferably a condensation reaction with the hydroxyl moieties. After a coating of the mixture is formed on the substrate, the mixture-coated substrate is separated from the mixture and cured, preferably by heating.

The second and preferred form of the surface-modifying polymer which is formed at the surface of the polymeric substrate is a polymeric material having pendant hydroxyl moieties. This surface-modifying polymer is formed and covalently bonded to the surface of the substrate by a grafting procedure. Such procedure includes treating the polymeric substrate with a solution of a suitable hydroxyl-containing polymerizable unsaturated monomer, typically a monounsaturated monomer having at least one hydroxyl group, and thereafter exposing the treated substrate to ionizing radiation, preferably gamma radiation. Polymerization of the monomer and grafting to the polymeric substrate results, yielding a polymeric substrate bearing a surface rich in hydroxyl groups and having a low affinity for protein. Preferred as monomers to form the surface-modifying polymers are hydroxyl-containing vinylic-type monomers, such as hydroxyalkyl acrylates and methacrylates.

This substrate is then reacted with a polyfunctional activating agent, preferably a polyfunctional acid halide or pseudohalide, to form a chemically activated porous, polymeric medium. This can subsequently be reacted with an acceptor molecule to form a medium which may be used as a diagnostic test medium, filter material or chromatographic support.

To form the medium which contains the acceptor molecule, also called the "biologically activated" or "biologically active" medium, since the acceptor molecule is typically a biological material, the chemically activated medium is reacted with the acceptor molecule under suitable reaction conditions. When the medium is intended as a diagnostic medium, the acceptor molecule constitutes a test reagent. To perform diagnostic tests, the diagnostic medium which includes the test reagent bound thereto is contacted with a fluid suspected of containing the analyte.

With the biologically activated media of the present invention, adsorption of peptide group-containing substances by the diagnostic media is minimized at locations other than where the activating agent is intentionally bound (active sites). Thus, when used as a diagnostic medium, the sensitivity of diagnostic tests is generally increased. In addition, the biologically active media, i.e., filtration, chromatographic and diagnostic media formed from the chemically active media of the present invention, exhibit desirable flow characteristics which are quite similar to those of the untreated polymeric substrate from which they are prepared. However, as compared to the behavior of untreated porous substrates, the media of the present invention, because of the greatly reduced adsorption of peptide group-containing materials, such as proteinaceous materials, maintain the fluid flow properties for prolonged periods of time.

Furthermore, the preferred chemically activated media of the present invention, as exemplified by those media employing bisazolides of carbonic acid, particularly N,N-carbonyl diimidazole as activating agents, demonstrate a high resistance to hydrolysis. This results in a high degree of retention of both chemically and biologically active sites on the surface of the media after storage in humid environments.

Best Modes for Carrying Out the Invention

The media which are suitable for forming the chemically activated media of the present invention, as well as the chemically activated media themselves, have a low tendency to bind protein in a non-specific manner as measured by the Immersion Protein Binding Assay (IPBA). When tested by this procedure, substances which sorb no more than about 30 micrograms/cm$^2$ are considered, for purposes of the present invention to have a low affinity for amide containing-group materials, such as proteinaceous materials. Preferred are those media which sorb no more than about 20 micrograms/cm$^2$. The media preferred in the present invention include a porous polymeric substrate or matrix, modified at its surface with a second polymeric material rich in pendant hydroxyl groups to provide a low affinity for peptide group-containing materials and particularly proteinaceous materials. The affinity of the surface-modified polymeric medium for such materials is typically much lower than the polymeric substrate from which the medium is formed. There may also be covalently bonded to the porous medium, through the surface-modifying polymeric material, an acceptor molecule, such as a member of a biospecific complex, and possibly a test reagent, which is typically a biological material.

Definitions

The following definitions apply to terms used herein.

The term "proteinaceous materials" refers to compounds which contain a peptide linkage and includes proteins and polypeptides. The term may also include substances not primarily proteins but which have sterically accessible amide moieties or polypeptide fragments.

Terms such as "surface", "polymeric substrate surface", "media surface" or like terms, used in the singular or plural, are intended herein to include not only the gross surfaces, i.e., the external or outer surfaces, such as those which are exposed to view, but also the internal surfaces or those surfaces which define the pores of the polymeric substrate or medium. Thus, the substrate or media surface is that portion of the polymeric substrate or medium which is capable during use of being contacted by a fluid, particularly a liquid. As distinguished from the "polymeric substrate surface area", which refers to the area of both internal and external surfaces, the exposed planar dimensional area of the material is herein referred to as the polymeric substrate area.

The term "analyte" refers to a substance or substances being tested for or determined by a diagnostic procedure. The analyte may be a simple chemical compound or one of a macromolecular nature, and may be substances of biological origin.

The term "test reagent" or "diagnostic reagent" refers to a substance or material which is covalently bound to the medium and binds specifically to the analyte. The presence of an analyte is typically indicated by the appropriate detection and/or measurement of a chemical or physical property after reaction or complex formation between the analyte and a detection reagent. Properties which may be observed include color changes, radioactivity or enzyme reactions. The term "reagent" and like terms may also refer both to substances reacting directly with an analyte as well as to substances used to convert either another substance or the analyte to a substance suitable for providing an indication, typically an optical indication, of the presence of the analyte.

These terms like the term "analyte" include simple chemical substances, including elements and compounds, of an ionic or molecular nature as well as more complex or macromolecular structures, such as proteinaceous materials, and include substances of a biological nature, such as antigens, antibodies, enzymes, antibody-enzyme conjugates, haptens, receptors, lectins, DNA fragments, and the like as well as viruses and whole cells.

The analyte may also be one or more of the substances falling within the definition of a reagent. In the case of antibodies, test reagents and analytes may each be monoclonal or polyclonal antibodies. Additionally, the analyte may include drugs, peptides, cells, and organelles. A reagent may additionally include buffers, indicator molecules, and substrates for enzymes.

"Antigenic substances", as used herein, include antigens and haptens. In some instances the biologically active substance serving either as an acceptor molecule or ligand may also include polypeptides, albumins, globulins and amino acids.

The terms "biologically active substance""biologically active material", and also "biologically active media", or like terms, as used herein, refer to any substance which functions in the present invention as either an acceptor molecule or a ligand and which is capable of forming a biospecific complex, such as an immune complex, with another material. The term "biospecific complex", as used herein, means a complex formed between biologically active materials specific to one another, such as between an acceptor molecule and a ligand. Thus, a biologically active substance, for instance, an antibody, functioning as an acceptor molecue, may form a biospecific complex with another biologically active substance, termed herein a ligand, such as an antigen corresponding to the antibody, to form a biospecific complex which, in the instant example, may also be termed an immune complex. The same antibody (biologically active substance), when bound to a membrane forms a biologically active membrane, in which membrane the antibody now functions as an acceptor molecule which is capable of reacting with the same antigen (ligand) to form a biospecific complex. It should be noted that, in most instances, either member of a biospecific complex may be selected to serve as the acceptor molecule while the other member functions as a ligand.

The term "liquophilic" refers to the property of porous materials in which the material is wettable by liquids. The wettability or liquophilicity of a porous structure, e.g., a medium, membrane, etc., is a function of that structure's surface energy and the surface tension of the applied liquid. If the surface energy is at least as high as the surface tension of the liquid, that liquid will spontaneously wet the structure. For example, a porous structure having a surface energy of 72 dynes/cm or higher will be wetted by water which has a surface tension of 72 dynes/cm. Such a structure, therefore, tends to freely pass aqueous solutions, i.e., the membrane is "hydrophilic". The capability of a porous structure (membrane) to be wetted by a liquid can be determined by placing a drop of the liquid on the porous structure. The angle of contact provides a quantitative measure of wetting. A very high angle of contact indicates poor wetting and may be used to characterize a "liquophobic" material, while a zero angle of contact defines complete or perfect wetting. The term "hydrophobic" indicates poor wetting by or sorption of water. Materials used in the subject invention, including porous polymeric media, activated medium, and biologically activated media, are, preferably, wettable or liquophilic, i.e., they are readily or spontaneously wetted by the applied liquid and have a low angle of contact with the applied liquid.

The terms "activated medium", "chemically activated medium", "chemically active medium", "activated membrane", "chemically activated membrane", and like terms, refer to the product formed by the reaction of the medium or membrane and activating agent, whereby the activating agent is covalently bound to the low protein, surface modified medium.

Terms such as "monofunctional", "functional groups", "functionality", as used herein in describing the reactive groups of the monomer which makes it suitable for use in the embodiment of the present invention directed to a surface-grafted surface-modifying polymeric medium, refer to those functional groups which are believed to be responsible for polymerization and bonding to the polymeric substrate. Used in other contexts the term "functional groups" and like terms have their usual meaning.

The term "acid pseudohalide" refers to a moiety (or a molecule having such a moiety) which is chemically similar to an acid halide in its chemical reactions, in particular a moiety which acts as a reactive acylating agent in displacement reactions. In the present invention, the acid pseudohalides employed are di- or polyfunctional and resemble polyfunctional acid halides in their chemical behavior. Typically, the acid pseudohalides, which are employed as activating or linking agents in the present invention, react with hydroxyl groups present at the surface of the porus polymeric medium to form esters, in a manner similar to carboxylic acid halides.

The terms "specific binding", "specific protein binding", and like terms, refer to bonds formed between proteinaceous members of a biospecific complex involving both molecular forces, other than covalent forces, and the complementary mating of configurationally commensurate surfaces. The terms "non-specific binding", "non-specific protein binding", "binding in a non-specific manner" and like terms, refer to bonds formed between a peptide group-containing material, preferably a proteinaceous material, and another substance involving the same type of molecular forces but lacking the configurational interactions found in specific binding.

Porous Polymeric Medium

The porous polymeric media of the present invention are generally characterized as having a low affinity for peptide group-containing materials, particularly proteinaceous materials. The tendency to adsorb proteinaceous materials may be measured by the Immersion Protein Binding Assay discussed in greater detail below. The preferred porous polymeric media employed in the present invention include a porous polymeric substrate or matrix which has been modified at its surface with a second polymeric or surface-modifying material, either coated or grafted thereon, and having a high concentration of hydroxyl groups at its surface.

Polymeric Substances

The porous, polymeric substrates or matrices suitable for use in preparing the preferred media of the present invention are those materials which do not react adversely with either the compounds used to form the second or surface-modifying polymeric material at the surface of the polymeric substrate, solvents, or other reagents employed in preparing either the chemically or biologically activated media of the present invention nor, preferably, with those materials employed in performing diagnostic tests or separations. The substrates employed in the present invention typically exhibit moderate to high affinity for peptide group-containing materials, particularly proteinaceous materials. The substrates are, preferably, microporous, in the form of a membrane, and also skinless.

When the media are intended to pass liquids therethrough, materials which exhibit desirable flow properties are generally employed. Thus, liquophilic substrates are preferred and hydrophilic media are particularly preferred when aqueous solutions are used. Included among the desirable flow properties of a polymeric substrate employed in the present invention is a low blockage or resistance to flow, typically characterized by absolute pore ratings (pore diameters) in the range of about 0.05 to about 100 microns, preferably about 0.1 to about 30 microns. When a membrane is employed as the substrate, the preferred pore diameter range preferably corresponds to that of a microporous medium, typically about 0.05 to about 10 microns, preferably about 0.1 to about 3 microns.

The porous polymeric media of the present invention have thicknesses of about 0.001 to about 0.050 inch (about 0.025 to about 1.25 mm) and, when employed as filtration media, suitably have thicknesses of about 0.002 to about 0.020 inch (about 0.05 to about 0.50 mm), typically about 0.002 to about 0.010 inch (about 0.05 to about 0.255 mm). The voids volume (percentage voids) of materials primarily intended as filtration media are suitably about 30 to about 95 percent, typically about 50 to about 90 percent.

The high porosities and surface areas of the media of the present invention, as well as the low pressure drops across the media, permit procedures to be performed more rapidly and efficiently than other materials employed in similar applications.

In those media in which a second polymeric material is grafted to the surface of the polymeric substrate, the polymeric substrates employed are capable of forming radical species at their surfaces when exposed to ionizing radiation. Suitable polymeric substrates have C—H bonds available for abstraction of H atoms and radical formation under the influence of ionizing radiation.

Among the porous polymeric substrates which are typically employed in the present invention are melt spun webs and, because of their fine and uniform pore structure, membranes. The latter are preferred. These substrates normally exhibit a high affinity toward peptide group-containing materials, particularly proteinaceous materials. Examples of such materials are polyamides, polysulfones, and polyacrylonitrile. Among these materials, polymers preferred for use in the present invention are polyamides, such as the nylons, among which the preferred nylons include polyhexamethylene adipamide, poly-$\epsilon$-caprolactam, polymethylene sebacamide, poly-7-aminoheptanoamide, or polyhexamethylene azeleamide, with polyhexamethylene adipamide (nylon 66) being most preferred. Particularly preferred are skinless, substantially alcohol-insoluble, hydrophilic polyamide membranes These membranes are also characterized as having a ratio of methylene $CH_2$:amide NHCO within a range of about 5:1 to about 7:1.

The present invention may also use polymeric substrates which exhibit lower affinity to proteinaceous materials. Examples of such materials would include cellulose esters, such as cellulose nitrate, polyolefins, such as polyethylene and polypropylene, polyesters, such as polyethylene terephthalate and polybutylene terephthlate, and fluoropolymers, such as polyvinylidene difluoride.

Preferred as the porous polymeric substrates of the present invention are hydrophilic microfibrous webs made of polypropylene, polyethylene terephthalate, and polybutylene terephthalate and also polymeric substrates in the form of membranes described in U.S. Pat. No. 4,340,479, assigned to Pall Corporation and incorporated herein by reference. A membrane material of this description which is particularly useful for the present invention is available from Pall Corporation under the trademark ULTIPOR®N$_{66}$®.

Surface-Modifying Polymeric Material

The preferred porous polymeric media of the present invention have formed at the surface of the porous polymeric substrate a second polymeric material having a low affinity for peptide group-containing materials as determined by the Immersion Protein Binding Assay. It is the second polymeric material, which has a plurality of (pendant) hydroxyl groups, in combination with the polymeric substrate, which modifies the surface of the porous polymeric media to provide a low affinity for peptide group-containing materials, such as proteinaceous materials. Preferred as the second or surface-modifying polymeric material is a material which is grafted to the surface of the polymeric substrate. However, the preferred media of the present invention also include polymeric materials formed as a coating on the surface of the polymeric substrate.

Although not wishing to be held to any particular theory, it is believed that the hydroxyl moieties, present at and suitably oriented with respect to the surface of the porous, polymeric medium, lessen the attraction of peptide group-containing materials to the medium. Such attraction is much less than that of many employed for such purposes.

In addition to providing a low protein adsorbing surface, it is also believed that the plurality of hydroxyl groups present on the surface of the medium provide two additional functions in the present invention. Namely, it appears that the linking or activating agents employed in the present invention react with the hydroxyl groups to form covalent bonds to the polymeric medium, particularly the surface-modifying polymeric material. The presence of hydroxyl groups at the surface of the medium also provides hydrophilicity to those substrates which may be hydrophobic.

(a) Surface-Grafted Surface-Modified Low Protein Binding Polymeric Material

The material which is most preferred as the surface-modifying polymeric material in the preferred media of the present invention is one which is polymerized at the surface of the polymeric substrate and grafted thereto to provide a reduced affinity for proteinaceous materials. The surface-modifying polymeric material may be any polymeric material formed from a monofunctional unsaturated monomer rich in pendant hydroxyl groups or groups capable of reacting to form hydroxyl groups, particularly after or upon formation of the second polymeric material, and which is capable of undergoing polymerization and/or covalent bonding to the substrate under the influence of ionizing radiation. While not wishing to be bound to any particular theory, it is believed that under the influence of ionizing radiation unsaturated bonds in the monomer molecules enter into polymerization and cross-linking reactions with other monomers and into reactions which form bonds to the substrate. Particularly preferred is vinylic or ethylenic unsaturation. Monomers suitable for use in the present invention have but a single polymerizable functional group, that is, a single unit of unsaturation. However, while these monomers preferred in the present invention also have a single hydroxyl group, compounds with a plurality of hydroxyl groups are also suitable. Suitable as the surface modifying polymeric material are those materials which provide in the modified medium a low adsorption of proteinaceous material as measured by the Immersion Protein Binding Assay discussed in greater detail below. According to this test, polymers which adsorb no more than about 30 micrograms/cm$^2$ of proteinaceous material are considered, for purposes of the present invention, to have a low affinity for proteinaceous materials, and materials adsorbing no more than about 20 micrograms/cm$^2$ are preferred. Conversely, for purposes of the present invention, polymers which adsorb more than about 30 micrograms/cm$^2$ of proteinaceous material are considered to have a high affinity for proteinaceous material.

The preferred polymeric material which forms the modified surface of the medium is derived from monomers having moieties characterized by ethylenic or vinylic unsaturation and hydroxyl groups. However, preferred compounds may additionally include other groups, such as carboxylate moieties, hydroxyl or hydroxyl-forming substituted acrylate esters being exemplary. Particularly preferred as monomers are hydroxyalkyl acrylates and methacrylates in which the "alcoholic" or hydroxyl-containing portion of the molecule, that is, the hydroxyalkyl group, constitutes a hydroxyl-substituted lower alkyl group having from 2 to 5 carbon atoms, preferably from 2 to 3 carbon atoms. Although the preferred substituent is a hydroxyl group, a substituent capable of reacting to form a hydroxyl group may be present Mixtures of monomers may also be used. The hydroxyl-containing monomers and/or the hydroxyl-containing polymeric material formed therefrom which are most preferred are those in which the hydroxyl group is present only as pendant hydroxyl groups. By "pendant" is meant the group is not attached to a carbon atom which forms part of the polymer's backbone but is bound to a carbon atom that is separated from the backbone as, for example, a branching carbon atom. This may be contrasted with materials of natural origin such as cellulose and agarose in which hydroxyl moieties are present as pendant hydroxyl groups as well as those hydroxyl groups which are located on adjacent or vicinal carbon atoms Exemplary of preferred monomers are such compounds as 2-hydroxyethyl acrylate, 2-hydroxyethyl methacrylate, hydroxypropyl acrylate, and hydroxypropyl methacrylate The hydroxypropyl acrylate and methacrylate are available commercially as isomeric mixtures of the 2-hydroxyprop-1-yl and 1-hydroxyprop-2-yl esters. These compounds are available commercially from Rohm and Haas Chemical Company under the trademark ROCRYL and are designated ROCRYL 410, 400, 430, and 420, respectively Alternatively, these and other compounds suitable for use in the present invention may be obtained either from commercial sources or may be prepared by reactions and techniques known to the organic chemist In addition to the structural features designated above, suitable monomers may be further characterized by their properties, such as interaction with ionizing radiation to form a free radical. Suitable monomeric compounds should also be substantially completely, if not totally, soluble in the solvent systems employed. The solvent should maximize solubility, not adversely affect the polymeric substrate nor the monomer employed, while permitting a satisfactory polymerization. Preferred solvents include polar solvents, particularly hydroxylated solvents such as water, lower aliphatic alcohols, such as ethanol, and mixtures thereof.

Solutions of the monomer compound are used in amounts sufficient to provide low affinity for peptide group-containing materials but without blocking the pores of the medium. Typically the amounts used in the present invention range in concentration of the monomer(s) from about 0.1 to about 5.0 percent, by weight, preferably about 0.2 to about 3.0 percent, by weight, based on the total weight of solution. The concentration of the second or surface-modifying polymeric material and, therefore, the concentration of the monomer used to form the surface-modifying polymeric material is selected so as to provide the porous polymeric medium with a substantially lower affinity for proteinaceous materials. However, a concentration sufficiently high to result in "plugging" of the substrate so as to adversely affect the flow properties of the media is to be avoided.

Polymerization and grafting of the monomer may be accomplished using ionizing irradiation with such sources as U.V. light or a cobalt 60 source, preferably the latter. The particular methods employed are discussed by Gsell U.S. patent application Ser. No. 945,569 Dec. 23, 1986 which is specifically incorporated herein by reference.

Hydrophilic porous polymeric media produced according to the present invention demonstrate high fluid-permeability. More significantly, however, as the examples show, these media have protein adsorption levels, as determined by the Immersion Protein Binding Assay, of about 50% to about 1%, typically about 20% to about 1.5%, of the untreated substrate.

(b) Coated Surface-Modified Low Protein Binding Polymeric Material:

The polymer coating having low affinity for peptide group-containing materials, particularly proteinaceous materials, which is formed at the surface of the polymeric substrate, may be any polymer which demonstrates a low adsorption of peptide group-containing material, such as proteinaceous material, as measured by the Immersion Protein Binding Assay discussed in greater detail below.

Like the surface-grafted, surface-modifying polymeric material, the coated surface-modifying polymeric material is rich in hydroxyl groups or groups which are capable of reacting to form hydroxyl groups, particularly after or upon formation of the polymeric coating. Typically, such low affinity polymers are cross-linked polymers that are rich in hydroxyl groups, preferably liquophilic and particularly preferred are polymers which are hydrophilic. The polymeric coating is formed, preferably, by a condensation reaction and preferably by the reaction of a polymer which contains a plurality of hydroxyl moieties with a cross-linking agent. The hydroxyl moiety-containing polymers which are most preferred are those in which the hydroxyl group is pendant. By "pendant" is meant the group is not attached to a carbon atom which forms part of the polymer's backbone but is bound to a carbon atom that is separated from the backbone as, for example, a branching carbon atom.

The hydroxyl moiety-containing organic polymer reacts with a cross-linking agent containing moieties which are capable of reacting with hydroxyl moieties. To establish cross-linking, the hydroxyl moiety-containing polymer includes at least two hydroxyl groups capable of reacting with moieties on the cross-linking agent which itself contains at least two moieties capable of reacting with a hydroxyl moiety. The cross-linking agent used to form the polymeric coating may be either monomeric or polymeric, preferably the latter. Both the cross-linking agent and the hydroxyl moiety-containing polymer are, preferably, substantially soluble in the solvent employed. Typically, at the concentrations employed, there will remain undissolved no more than about 1% hydroxyl moiety-containing polymer, based on the weight of the hydroxyl moiety-containing polymer employed. Likewise, there ill typically not be more than about 1 percent undissolved cross-linking agent, based on the weight of the cross-linking agent employed In addition, the hydroxyl moiety-containing polymer should not have an excessively high molecular weight. Typically, the hydroxyl moiety-containing polymer has a weight average molecular weight of no more than about 500,000, and preferably greater than about 10,000. Examples of suitable hydroxyl moiety-containing polymers include cellulose derivatives, such as cellulose acetate and other alkyl esters of cellulose; and hydroxyalkyl esters of cellulose, such as hydroxypropyl cellulose and hydroxyethyl cellulose; carboxylated alkyl cellulose, such as carboxymethyl cellulose; hydroxyalkyl esters of acrylic acid and methacrylic acid, such as polyhydroxyethyl methacrylate; polyvinyl alcohol and modified starches. Preferred are the hydroxyalkyl esters of cellulose with hydroxypropyl cellulose being most preferred.

The cross-linking agent contains at least two moieties or is capable of forming at least two moieties, the same or different, which will react with the hydroxyl moieties of the hydroxyl moiety-containing polymer under reaction conditions, according to reactions known to the organic chemist. Examples include compounds having acidic moieties, such as carboxylic acid groups and phenolic groups; other compounds containing hydroxyl groups and particularly those containing $CH_2OH$ groups such as methylol compounds and particularly those in which the hydroxyl-bearing carbon is bound to a nitrogen atom; resoles; amide groups; and aldehydes, such as formaldehyde and glutardialdehyde. As indicated above, the cross-linking agent contains or forms during reaction at least two such moieties capable of reacting with hydroxyl groups. When the cross-linking agent is a polymer, examples of preferred polymers capable of reacting with the hydroxyl moiety-containing organic compounds are copolymers of acrylic acid and acrylamide, copolymers of acrylic acid and N-methylol acrylamide and polyacrylic acid.

Typically, and preferably, when the hydroxyl moiety-containing polymer contains a large number of hydroxyl groups, such as found in cellulose-derived polymers, after reaction with the cross-linking agent, there will be an excess of unreacted hydroxyl moieties in the polymer coating having low affinity for proteinaceous material.

The procedure for applying the mixture of hydroxyl moiety-containing organic polymer and crosslinking agent to the substrate, drying, and curing are described by Gsell in U.S. patent application Ser. No. 945,867, filed on Dec. 23, 1986, specifically incorporated herein by reference.

Chemically Activated Media

The activated media of the present invention, typically in the form of a membrane, have a low tendency to sorb peptide group-containing materials, such as proteinaceous materials, in a non-specific manner, as measured by the IPBA. Preferred media include a polymeric substrate and a surface-modifying polymeric material having bound to the media a residue of an activating agent with moieties which are capable of readily reacting with an acceptor molecule. Typically, the acceptor molecule is a biological material, such as a test reagent, and preferably a proteinaceous material.

Reaction of an activating agent with the low protein binding porous polymeric media described above, preferably in the form of membranes, results in the formation of activated or chemically activated media which have activating agent residues covalently bound to the media which include groups or moieties active toward or capable of reacting with a ligand, also typically a biological and proteinaceous material.

The particular procedure employed in forming the activated medium will depend, in large part, on the choice of the activating agent to be employed. The activating or linking agents suitable for use in the present invention are discussed below and particular procedures for their use are described adequately in the scientific literature. Generally, to prepare the activated media of the present invention, the medium is placed in a suitable container in contact with a solution of the activating agent selected and an appropriate solvent suitable to dissolve the activating or linking agent and any other reagents required for the reaction occurring between functional groups on the surface of the medium material and the activating agent.

A stable activated medium is the product formed by the reaction of the medium and activating agent. It is this activated medium in which a residue of the activating agent is covalently bound to the medium which allows the acceptor molecule to be immobilized or bound to the membrane by a covalent bond to form the biologically active media of the present invention. Suitable activating agents comprise substances which include at least two functional groups, one functional group being capable of reacting with reactive moieties at the surface of the medium, such as hydroxyl moieties on the surface-modifying polymeric material, to form a membrane having functional groups at its surface which are chemically reactive with an acceptor molecule, such as biologically active materials. These functional groups result from the residues of the covalently bound activating agents having at least one remaining functional group.

The first functional group of the activating agent which reacts with reactive moieties at the surface of the medium leaves a radical or residue of the activating agent bound to the membrane which contains one or more remaining functional groups. For example, in the case of an activated medium which employs T-s-T (trichloro-s-triazine) as the activating agent, the s-triazine moiety still includes reactive chlorine atoms bound to each s-triazine radical or residue, which residue is covalently bound to the membrane. Each of these s-triazine bound chlorine atoms is capable of reacting with an acceptor molecule, such that the latter becomes covalently bound to the membrane through the s-triazine residue. Activating agents of this type thus serve to activate the membrane in a first reaction and function as a linking agent by coupling an acceptor molecule to the membrane through a residue of the activating agent in a second reaction.

Suitable materials to be used as the activating agent in the present invention are any of the materials generally known and used in the art for the same or similar purposes. These include compounds having at least two functional groups, at least one of which is capable of reacting with a hydroxyl group such as that present on the surface of the media of the present invention which have a small tendency toward non-specific binding of peptide group-containing materials such as proteinaceous materials. The hydroxyl groups are preferably bound to the surface-modifying polymeric material of the porous polymeric medium preferred in the present invention. Examples of preferred materials for use in the present invention as activating agents include, but are not limited to cyanuric acid halides, such as trichloro-s-triazine (T-s-T) and substituted dichloro-s-triazines; dicarboxylic acid derivatives including dicarboxylic acid dihalides, such as adipyl chloride and terephthaloyl chloride, pyridine-2,5-dicarbonyl chloride, diazides of dicarboxylic acid, dicarboxylic acid bisimidazolides, such as pyridine-2,5-dicarboxylic acid bisimidazolide, terephthalic acid bisimidazolide, and sebacic acid bisimidazolide; sulfonic acid dihalides, such as benzenedisulfonyl chloride; carbonic acid derivatives, such as phosgene, N,N'-diphthalimidocarbonate, N,N'-disuccinimidylcarbonate, di-2-pyridylcarbonate, N,N'-carbonyldi-1,2,4-triazole, N,N'-carbonyldi-1,2,3-triazole, and N,N'-carbonyldiimidazole.

Preferred as activating agents are those which provide residues in activated media which not only show a tendency to bind large numbers of acceptor molecules in a specific manner but also demonstrate a resistance to hydrolysis of the remaining functional groups on the activating agent residue. Such activating agents also show a high resistance to hydrolysis of the biologically active media. The high resistance to hydrolysis is indicated by a high value in the "Accelerated Moisture Exposure Test" (AMET) set forth below. For example, a membrane prepared with N,N'-carbonyldiimidazole has demonstrated a retention of covalent binding capacity of about 80%. Preferred as activating agents demonstrating a high capacity to bind acceptor molecules, such as proteins, in a specific manner and a high resistance to hydrolysis include bisazolides of carbonic acid, preferably N,N'-carbonyldi-1,2,4-triazole, N,N'-carbonyldi-1,2,3-triazole, and N,N'-carbonyldiimidazole, with the last mentioned compound being most preferred.

The activated media employing the other activating agents tend to hydrolyze in the presence of moisture resulting in fewer active sites to bind to acceptor molecules. In contrast, the activated media which employ N,N'-carbonyldiimidazole and the bisazolides of carbonic acid demonstrate a high hydrolytic resistance and, therefore, long shelf lives.

For the formation of an activated medium, typically in the form of a membrane, the membrane is contacted with a solution which contains the activating or linking agent, and, optionally a tertiary amine and an acylation catalyst. Typically, the membrane is exposed to the linking agent, base, and catalyst simultaneously. When the linking agent is a polyfunctional acid halide, it is preferred that a base is present in the solution. When the linking agent is an azolide or an imidazolide, it is preferred that the solution does not contain the base. Typically, concentrations for both the linking agent and the base, when employed, are from about 0.01 molar to the limit of solubility in the particular solvent used provides satisfactory results. It is preferred that concentrations of each be about 0.05 molar to about 0.20 molar and that the base and linking agent be present in equimolar amounts. To effect reaction with the surface of the medium, the membrane is maintained submersed in the reaction solution or, alternatively, the reaction solution is passed through the membrane, generally at ambient temperature, for a period sufficient to effect substantial reaction between the activating agent and the functional groups on the surface of the membrane.

The number of chemically active sites formed on the surface of the membrane varies directly not only with the concentration of activating agent and base, but also with the duration of reaction time between the surface modified medium and the activating agent. The reaction period is typically about five minutes to about two hours and preferably, when a submersion technique is used, is about five minutes to about one hour. It is also preferred, when a submersion technique is employed, that agitation be employed to assure adequate contact during the activation step between the reaction solution and the membrane material. The reaction solution is then decanted from the immersed membrane, which may be further washed to remove unreacted reagents. The preferred wash medium is generally the liquid which is used as the solvent or medium for the reaction solution or, alternatively, may be other suitable solvents. Generally, the activated membranes are thereafter dried and may then be used to form the biologically activated supports described below.

Solvents suitable for use in the activation reaction are those capable of dissolving both the organic base and linking agent, and include methylene chloride, dioxane, tetrahydrofuran, acetone, or the like. Particularly preferred is methylene chloride because of high volatility which allows, therefore, its facile removal, and, additionally, because of its low flammability.

Organic bases suitable for use are preferably tertiary amines, including diisopropylethylamine, triethylamine, diisopropylmethylamine, dimethylaniline, and pyridine Particularly preferred as the organic base is triethylamine because of its availability and low cost.

In some instances, the solution of linking agent may also include an acylation catalyst Suitable catalysts include but are not limited to pyridine, triethylamine, and 4-dimethylaminopyridine (DMAP).

Biologically Active Media

The biologically activated media of the present invention, as indicated above, are derived by reacting as an acceptor molecule, under conditions suitable to effect reaction, with the chemically activated media of the present invention to covalently bind the acceptor molecule to the porous polymeric medium through a residue of a linking or activating agent. Immobilization results from covalent bonds formed between one or more of the remaining functional groups of the residue of the activating agent on the membrane surface and a functional group of the acceptor molecule. The covalent bonds between the acceptor molecules and the residue of the activating agent obviate bleeding or leaching of the acceptor molecules from the medium. Since the acceptor molecules from the medium. Since the acceptor molecule is typically, and in most instances preferably, of a biological nature, a biologically active medium results. While the media are described herein in terms of "biolgically active media" and preferably include as acceptor molecules macromolecular and biologically active materials, it should be understood that test reagents and analytes which are "simpler" chemical compounds or are of a non-biological nature may in some instances also be used.

The present invention is expected to have widespread application to biospecific complexes which, as indicated above, are formed between an acceptor molecule and a ligand, typically as between biologically active materials. The substances which form at least one member of the biospecific complexes of the present include, most preferably and frequently, proteins. The type of substances which may serve as the biologically active acceptor molecules and those substances which function as the corresponding ligands in the biospecific complexs according to the present invention are listed in Table 1.

TABLE 1

| Biospecific Complexes | |
|---|---|
| Acceptor Molecule | Ligand |
| Polyclonal antibody | Antigenic substance |
| Monoclonal antibody | Antigenic substance |
| Antigenic substance | Polyclonal antibody |
| Antigenic substance | Monoclonal antibody |
| Glycoprotein | Lectin |
| Protein A | IgG class immunoglobulin |
| Lectin | Carbohydrate |
| Lectin | Glycoprotein |
| Carbohydrate | Lectin |
| Enzyme substrate | Enzyme |
| Co-factor | Enzyme |
| Inhibitor | Enzyme |
| Hormone | Carrier protein |
| Hormone | Receptor |
| Carrier protein | Hormone |
| Receptor | Hormone |
| Heparin | Coagulation factor |
| Coagulation factor | Heparin |
| Histone | Nucleic acid |
| Histone | Polynucleotide |

To form the biologically active medium of the present invention, particularly in the form of a membrane, the procedure described by Degen et al in U.S. Pat. No. 4,693,985 and specifically incorporated herein by reference, may be followed. The European Patent Office cognate is EPO Application No. 853305655.4 (Publication No. 0173500 )

The number of chemically activated sites (i.e., sites occupied by residue of an activating agent with unreacted functional moieties) remaining on a biologically active medium may vary depending upon the application and acceptor molecules employed by the user. For example, some monoclonal antibodies may be quite expensive, and since only a small amount need be covalently bonded to the medium through the activating agent to obtain suitable test results, less than the full number of chemically activated sites need to have the antibody bound thereto. However, were there to be activated sites remaining when additional proteinaceous material was added, such as when a test sample potentially containing analyte were to contact the medium, the remaining activating sites would bind both specific and non-specific protein. This potentially could have an adverse affect on the test results. Depending upon the application of the medium and the number of chemically active sites, it may be desirable in some instances to deactivate or block the remaining chemically active sites to prevent reaction with additional protein. This may be accomplished by treating the biologically active medium containing some chemically active sites with either a blocking agent or a deactivating agent. Blocking agents are typically compounds of a proteinaceous nature or, in some instances, detergents which may bind to the medium either by chemical or by physical interactions, typically the former type of interaction at chemically active sites and the latter where little or no surface modification to impart low protein binding properties exists. Examples of such blocking agents include casein, Bovine Serum Albumin, gelatin, and detergents or surfactants, such as Triton X-100 and Tween 20. Deactivating or "capping" agents include those materials which react chemically with the functional groups at the active sites. Examples of such compounds include amines such as ethanolamine and diethanolamine, amino acids such as glycine and polyhydric lysine.

Binding a Ligand Specific to the Acceptor Molecule Immobilized on Biologically Active Membrane The biospecific adsorption or attachment of a ligand, such as an antigen, hapten, antibody or the like, to the biologically active medium, particularly in the form of a membrane, may be accomplished by contacting or passing a solution of an appropriate ligand through the biologically active membrane. A suitable procedure ,may be found in U.S. Pat. No. 4,693,985 . This application also describes suitable means of detection of the analyte.

EXAMPLES

Example I(a)

Preparation of a Porous Polymeric Medium Having a Surface-Grafted

Surface-Modifying Polymeric Material:

An aqueous solution of 3-hydroxypropyl acrylate (HPA) (Rocryl TM 430 from Rohm and Haas) was prepared by adding 2 parts HPA to a solvent system containing, by volume, 96 parts of deionized water and 2 parts tertiary butyl alcohol. The solution was stirred until uniformly mixed, producing a 2%, by volume, concentration of HPA.

A 200 foot long×10 inch wide roll of microporous nylon 66 (ULTIPOR ®$N_{66}$®, available from Pall Corporation) was contacted with the 2.0 volume percent solution of hydroxypropyl acrylate. The microporous nylon substrate, in roll form, was immersed in the monomer solution and allowed to become completely saturated. No attempt was made to remove excess solution from the roll. The saturated roll was transferred to and sealed in an irradiation chamber, specifically a stainless steel vessel having a wall thickness of 0.030 inch.

The roll was exposed to gamma radiation at a dose rate of 25,000 rads/hour for a total of 60 hours for a total dose of 1.5 megarads. The roll was then removed from the vessel and washed to remove residual monomer and ungrafted polymer by allowing deionized water to circulate around the roll for 24 hours. A small section of medium was removed from the roll, clamped in a frame, and dried for 15 minutes at 100 degrees C. for subsequent testing.

Example I(b)

Preparation of a Porous Polymeric Medium Having a Coated Surface-Modifying Polymeric Material A solution used to form a polymer coating having a low affinity for proteinaceous material was prepared by adding 40 grams of CARBOSET 531 (a thermosetting copolymer of acrylic acid and N-methylol acrylamide containing 25 percent solids) to a stirred solution of 1,910 grams of deionized water containing 50 grams of tertiary butyl alcohol. After approximately 10 minutes of mixing, during which the CARBOSET 531 had fully dissolved, 20 grams of Klucel LF (hydroxypropyl cellulose, available from Hercules) was added with continued stirring. After approximately 3 hours of continuous stirring, the Klucel was fully dissolved and the solution was filtered through a filter membrane of ULTIPOR N66 (a registered trademark for a microporous, hydrophilic nylon 66 filter media available from Pall Corporation) having an absolute removal rating of 0.1 micron, to remove any residual solid material. The coating solution contained about 1.0 weight percent, based on the total weight of solution of hydroxypropyl cellulose, and about 0.5 weight percent of acrylic acid/N-methylol acrylamide copolymer.

A 9 inch by 9 inch sheet portion of a microporous hydrophilic nylon 66 membrane (ULTIPOR ®$N_{66}$®, available from Pall Corporation, having a 0.2 micron absolute pore rating) was contacted with the monomer coating solution for a period o about 5 seconds. The membrane was removed from the coating solution and excess fluid was blotted from its surface. Clamped to a frame, the membrane was placed in a recirculating air oven at a temperature of 150° C. for a period of 30 minutes.

Example II

Preparation of a Porous Polymeric Medium Activated With Terephthaloyl Chloride

A solution of activating agent was prepared by adding 1.8 g terephthaloyl chloride, while stirring, to 125 ml methylene chloride. After cooling to near 0° C., 2 ml triethylamine was added followed by 0.11 g 4-dimethyaminopyridine (DMAP).

The mixture was filtered through a #42 Whatman filter paper. The temperature of the solution was raised to 25° C. and a 6 square inch portion of a membrane prepared according to Example I(a), having a pore size of 1.2 microns was immersed in the solution of activating agent. The membrane was agitated gently in the solution for a period of 1 hour, after which the solution was removed and the membrane was washed by agitation for 5 minutes each in four successive 100 ml portions of methylene chloride. The activated membrane was dried in an air oven at 60° C. for 2 minutes and was thereafter stored in a desiccator for later use.

Example III

Preparation of a Porous Polymeric Medium Activated with 2,5-Pyridine Dicarbonyl Chloride A solution of activating agent was prepared by adding 1.8 g 2,5-pyridine dicarbonyl chloride, while stirring, to 125 ml methylene chloride. The mixture was filtered through a number 42 Whatman filter paper and cooled to near 0° C. Two ml triethylamine was added followed by 0.11 g 4-dimethylaminopyridine. The temperature of the solution was raised to 25° C. and a 6 square inch portion of a membrane prepared according to Example I(a), having a pore size of 1.2 microns was immersed in the solution of activating agent.

The membrane was agitated gently in the solution for a period of 1 hour, after which the solution was removed and the membrane washed by agitation for 5 minutes each in four successive 100 ml portions of methylene chloride. The activated membrane was dried in an air oven at 60° C. for two minutes and was thereafter stored in a desiccator for later use.

Example IV

Preparation of a Porous Polymeric Medium Activated with N,N'-Carbonyldiimidazole A solution of activating agent was prepared by dissolving 0.49 g of N,N'-carbonyldiimidazole in 45 ml methylene chloride. A 3 square inch portion of the material prepared in Example I was immersed in the solution of activating agent for 15 minutes at ambient temperature. After removal of the solution from the membrane, washing was accomplished by agitating the membrane with four 40 ml portions of methylene chloride for a period of 5 minutes each. The membrane was dried in an air oven at a temperature of 60° C. for 3 minutes and afterward stored in a desiccator for further use.

Example V(a)

Preparation of a Porous Polymeric Medium Activated with N,N'-Carbonyldiimidazole The procedure and materials outlined in Example IV were employed in the preparation of an activated membrane. In addition to the reagents employed in Example IV, however, 0.11 g of DMAP was added.

Example V(b)

Preparation of a Porous Polymeric Medium Activated with N,N'-Carbonyldiimidazole The same materials employed in Example V(a) were used in the following amounts: 0.54 g N,N'-carbonyldiimidazole, 0.12 g DMAP, and 45 ml methylene chloride and a 1.5 inch×2 inch strip of the surface-grafted, surface-modifying polymeric material prepared according to Example I(a), was immersed in the solution of activating agent. Immersion, with occasional agitation, was performed at ambient temperature for two hours rather than a 15 minute period as in Example V(a). The membrane material was then washed with four 40 ml portions of fresh methylene chloride, allowing the membrane material to remain in the wash for 5 minutes for each portion. The membrane material was dried in an oven at 60° C. for 3 minutes.

Example VI

Preparation of a Porous Polymeric Medium Activated with Trichloro-s-triazine

A solution of activating agent was prepared by adding 0.011 g DMAP and 5 ml dimethylformamide in that order, to a solution of 2.5 g trichloro-s-triazine and 2.5 ml triethylamine in 45 ml methylene chloride. A 3 in² portion of Loprodyne (a trademark of Pall Corporation, the material prepared according to Example I) was placed in the solution of activating agent for a period of 45 minutes at ambient temperature. The membrane was thereafter washed, dried and stored for further use as described in Example IV.

Example VII

Measurement of Protein Binding

The activated membranes prepared according to Examples I(a) and II–VI were tested for their abilities to covalently bind the protein goat immunoglobulin G (goat IG) according to the general procedure for measuring protein binding outlined below.

Immersion Protein Binding Assay

A 13 mm diameter disc of the membrane being tested was immersed in 2 ml solution of a labelled protein containing solution prepared by combining 200 microgram/ml goat IgG (Sigma Chemical Company product no. RA-5256) and 121,000 counts per minute $^{125}$I-labelled goat IgG (New England Nuclear product no. NEX-155) in phosphate buffered saline solution (PBS). The biological protein material in PBS was adjusted to a pH of 7.0 with a solution containing 0.15 moles/liter sodium chloride and 0.02 moles/liter of a mixture of mono-, di-, and trisodium phosphate. In those situations in which more than one membrane was tested at the same time, all membranes were immersed in the same portion of solution, the volume of the total solution adjusted to provide 2 ml of solution per 13 mm disc.

The discs were agitated in the solution for a period of one hour, after which the IgG solution was decanted and the remaining liquid was removed from the immersion vessel using a pipet. PBS solution was added to the immersion vessel in the same volume as the previously used biological material-containing solution (2 ml per disc) and the membranes were agitated in the solution for 5 minutes to wash and remove residual protein. The wash solution was decanted and the washing procedure was repeated twice using fresh PBS solution each time for a total of three washes. The membrane discs were then removed, blotted gently between absorbent paper and the residual activity was counted using a LKB Wallac Mini Gamma Ray Counter, model no. 1275. The amount of radioactive material on the disc is a measurement of the total protein bound to the discs, i.e., both covalently bound protein and that which is present because of strong non-specific adsorption. This protein is referred to as "post PBS protein".

To determine the amount of protein that is covalently bound to the membranes, the discs were washed twice for 15 minutes each in an aqueous solution containing 2 moles/liter urea and 1%, by weight, of sodium dodecyl sulfate (SDS). The washing was continued in the same manner as with PBS, using 2 ml solution per disc. After washing, the discs were blotted dry between absorbent paper and residual radioactivity was counted using the gamma ray counter. The amount of protein measured on the discs at this time is referred to as "post SDS protein" and is a measure of the amount of protein which can be covalently bound or otherwise linked in a permanent fashion to the membrane substrate. The difference between the amount of post PBS protein and the amount of post SDS protein, i.e., that amount of protein which is removed by the SDS wash, is a measure of the protein which was non-specifically bound to the medium.

Table II presents information for both unactivated porous polymeric media (Example I(a)) as well as for membranes having high levels of protein covalently bound thereto (Examples II–VI). The post SDS treatment data indicates that a process of chemical activation according to the present invention enables inherently low protein-binding porous polymeric media (of the type illustrated by Example I) to permanently bind large amounts of any desired protein (as with Examples II–VI). This effect is clearly illustrated by the activation ratio, which is the ratio of the amount of protein covalently bound by the membranes of this invention to the amount of protein bound by the same unactivated porous polymeric medium.

It can also be seen from Table II that the chemically active media of this invention (Examples II–VI) bind proteins almost entirely at the activated sites and show little increase in non-specific affinity for proteins over the unactivated porous polymeric medium from which these media were made.

The usefulness of the low non-specific binding in conjunction with high levels of covalent protein binding is illustrated by what is referred to as "signal-to-noise ratio" (S/N). This ratio is the ratio of the amount of covalently bound protein (i.e., protein linked by intent to the medium and capable of leading to a positive signal in a diagnostic test) to the amount of non-specifically adsorbed protein (i.e., potentially undesired material adsorbed to the medium and which is capable of leading to a false signal-noise in a diagnostic test). The signal-to-noise ratio is, therefore, an indication of the potential sensitivity of a diagnostic test or biochemical assay carried out using a device made from the media of this invention. The higher the signal-to-noise ratio the greater the potential sensitivity of the test.

TABLE II

| Membrane of Example | Activating Agent | Covalent Binding ($\mu g/cm^2$) | Activation Ratio | Nonspecific Binding ($\mu g/cm^2$) | **S/N Ratio |
|---|---|---|---|---|---|
| I(a) | none | 2 | 1 | 6 | 0.3 |
| II* | terephthaloyl chloride | 22 | 11 | 5 | 4.4 |
| III* | 2,5-pyridine dicarbonyl-chloride | 33 | 16.5 | 13 | 2.5 |
| IV | N,N'—carbonyl bisdiimidazole | 37 | 18.5 | 10 | 3.7 |
| V(a)* | N,N'—carbonyl bisdiimidazole | 56 | 28 | 11 | 5.1 |
| V(b)* | N,N'—carbonyl diimidazole | 70 | 35 | 19 | 3.7 |
| VI* | TST | 77 | 38.5 | 20 | 3.8 |
| VII | Control Immunodyne TM) | 38 | N/A | 32 | 1.2 |

*(DMAP added)
**(i.e., ratio of covalently to non-specifically bound protein)

The material used as a control, designated as Example VII, is Immunodyne TM, a material available from Pall Corporation and described in U.S. Pat. No. 4,693,985. This membrane employs a nylon 66 membrane having the residue of T-s-T bound to its surface but having no surface-modifying polymer on the nylon to impart low non-specfic protein binding properties to the membrane.

As can be seen from the protein binding data in Table II, the media of this invention are capable of binding in a permanent manner nearly 40 times the amount of protein which is sorbed by the unactivated porous polymeric medium.

All of the biologically activated membranes of the present invention exhibit the ability to selectively bind acceptor molecules, generally of a proteinaceous nature, while sorbing relatively little peptide group-containing material at sites on the surface of the medium other than active sites, thereby producing a high selectivity and sensitivity in the medium. However, the media of the present invention, which are most preferred are those employing pseudohalide, the preferred activating agents, and particularly the bisazolides of carbonic acid with N,N'-carbonyl diimidazole being particularly preferred. The activated media prepared with these activating agents not only provide the aforementioned desirable attributes, but additionally retain their ability to covalently bind acceptor molecules, particularly proteins, and the so-prepared biologically activated media also retain their increased sensitivity. In contrast, chemically activated media prepared with other activating agents characteristically lose their capacity to covalently bind protein if not stored under moisture-free conditions. The resistance to hydrolysis of the preferred activated media of the present invention obviates the need to take extreme precautions to maintain the media in a moisture-free environment.

Accelerated Moisture Exposure Test

To simulate exaggerated exposure to moisture during storage, a microporous membrane having high capacity to bind proteins covalently and low capacity to bind proteins in a non-specific manner was prepared according to the procedures described in Example V(a). Several 13 mm discs cut from the material were immersed in 100 ml distilled water at ambient temperature and were gently agitated in the liquid by means of a magnetic stirrer. After 3.5 hours in the water, the discs were removed therefrom and their capacity to bind the protein was measured by means of the IPBA. Similarly, 13-mm discs of the control (Example VII) were stirred 3.5 hours in distilled water as a control and tested according to the general procedure for binding protein. The discs are compared with those not exposed to distilled water. The results of these tests are illustrated in Table III.

TABLE III

Hydrolytic Stability of Activated Membranes

| Exposure Time (hrs) | Membrane of Example | Covalent Binding ($\mu g/cm^2$) | % Retention of Covalent Binding Capacity | S/N Ratio |
|---|---|---|---|---|
| 0 | V(a) | 53 | — | 3.8 |
| 3.5 | V(a) | 43 | 81 | 2.7 |
| 0 | VII | 38 | — | 1.2 |
| 3.5 | VII | 20 | 53 | 0.4 |

The data presented in Table III illustrates that the preferred media of the present invention, those prepared with activating agents, the residues of which show a high resistance to hydrolysis according to the Accelerated Moisture Exposure Test, such as bisazolides of carbonic acid and particularly N,N'-carbonyl diimidazole, retain close to their original capacity to bind protein covalently after exposure to conditions representing an accelerated test of storage in a humid environment.

As can be seen in the S/N Ratio column, the prior art medium (Example VII) gives a S/N ratio of 0.4 which reflects increased non-specific protein adsorption due to the hydrolyzed activated sites. In sharp contrast, the preferred membrane of this invention (Example V(a)) provides a S/N ratio of 2.7, i.e., almost a sevenfold increase in sensitivity.

We claim:

1. A porous chemically activated medium comprising:
   a porous polymeric medium having a low affinity for peptide group-containing materials, as measured by the Immersion Protein Binding Assay, covalently bound to a residue of an activating agent said residue being capable of reacting with an acceptor molecule.

2. The chemically activated medium of claim 1 wherein said porous polymeric medium comprises a material rich in pendant hydroxyl groups.

3. The chemically activated medium of claim 2 wherein the porous polymeric medium comprises:
   (a) a porous polymeric substrate, and
   (b) a surface-modifying polymeric material having a low affinity for peptide group-containing materials formed at and covalently bonded to the surface of said porous polymeric substrate.

4. The chemically activated medium of claim 3 wherein said polymeric substrate comprises a material having C—H bonds capable of forming radicals under the influence of ionizing radiation.

5. The chemically activated medium of claim 3 wherein said surface modifying covalently bound polymeric material is formed from a monomer having at least one hydroxyl group.

6. The chemically activated medium of claim 5 wherein said monomer from which said covalently bound surface-modifying polymeric material comprises an ethylenically unsaturated compound.

7. The chemically activated medium of claim 3 wherein said porous polymeric substrate comprises a polyamide.

8. The chemically activated medium of claim 7 wherein said polyamide is nylon 66.

9. The chemically activated medium of claim 3 wherein said porous polymeric substrate comprises a hydrophilic material.

10. The chemically activated medium of claim 3 wherein said polymeric substrate is microporous.

11. The chemically activated medium of claim 1 wherein said peptide group-containing material comprises proteinaceous material.

12. The chemically activated medium of claim 1 wherein said medium has an adsorption of proteinaceous material measured by the Immersion Protein Binding Assay of no more than 30 micrograms per square centimeter.

13. The chemically activated medium of claim 5 wherein said monomer from which said surface-modifying covalently bound polymeric material is formed comprises a hydroxyalkyl acrylate or methacrylate.

14. The chemically activated medium of claim 5 wherein said monomer from which said surface-modifying covalently bound polymeric material is formed is 2-hydroxyethyl acrylate, 2-hydroxyethyl methacrylate, hydroxypropyl acrylate, or hydroxypropyl methacrylate.

15. The chemically activated medium of claim 5 wherein said monomer is 2-hydroxyprop-1-yl acrylate, 1-hydroxyprop-2-yl acrylate or mixtures thereof.

16. The chemically activated medium of claim 1 wherein said activating agent comprises a bisazolide.

17. The chemically activated medium of claim 1 wherein said activating agent comprises a bisazolide of carbonic acid.

18. The chemically activated medium of claim 1 wherein said activating agent comprises N,N'-carbonyldiimidazole.

19. The chemically activated medium of claim 3 wherein said porous polymeric substrate comprises nylon 66, the monomer from which said surface-modifying covalently bound polymeric material is formed is hydroxypropyl acrylate and the activating agent of which a residue is bound to the porous polymeric medium is N,N'-carbonyldiimidazole.

20. The chemically activated medium of claim 2 the porous polymeric medium comprises:
   (a) a porous polymeric substrate, and
   (b) a polymer coating having a low affinity for peptide group-containing materials formed at the surface of said porous polymeric substrate.

21. The chemically activated medium of claim 20 wherein said porous polymeric substrate comprises a polyamide.

22. The chemically activated medium of claim 21 wherein said polyamide is nylon 66.

23. The chemically activated medium of claim 20 wherein said porous polymeric substrate comprises a hydrophilic material.

24. The chemically activated medium of claim 20 wherein said polymeric coating is formed from a polymer having a plurality of hydroxyl groups and a cross-linking agent having functional groups which react with the hydroxyl groups.

25. The chemically activated medium of claim 24 wherein said cross-linking agent is a polymeric substance.

26. The chemically activated medium of claim 20 wherein said polymeric substrate is microporous.

27. The chemically activated medium of claim 24 wherein said hydroxyl group-containing polymer is hydroxypropyl cellulose.

28. The chemically activated medium of claim 24 wherein said cross-linking agent is a copolymer of acrylic acid and N-methylol acrylamide.

29. The chemically activated medium of claim 20 wherein said activating agent comprises N,N'-carbonyldiimidazole.

30. The chemically activated medium of claim 20 wherein said substrate comprises microporous, hydrophilic nylon 66 and said polymer coating is a product formed from the reaction of hydroxypropyl cellulose and a copolymer of acrylic acid and N-methylol acrylamide, and the residue of an activating agent comprises a residue of N,N'-carbonyldiimidazole.

31. A method of producing a chemically activated medium comprising reacting a porous polymeric medium having a low affinity for peptide group-containing materials, as measured by the Immersion Protein Binding Assay, with an activating agent to form a chemically activated medium.

32. The method of producing a chemically activated medium of claim 31 wherein said porous polymeric medium comprises a material rich in pendant hydroxyl groups including:
   a porous polymeric substrate, and
   a surface-modifying polymeric material having a low affinity for peptide group-containing materials formed at and covalently bonded to the surface of said porous polymeric substrate.

33. The method of producing a porous chemically activated medium of claim 32 wherein said polymeric substrate comprises a material having C—H bonds capable of forming radicals under the influence of ionizing radiation.

34. The method of producing a porous chemically activated medium according to claim 32 wherein said porous polymeric substrate comprises a polyamide.

35. The method of producing a porous chemically activated medium according to claim 32 wherein said polyamide is nylon 66.

36. The method of producing a porous chemically activated medium of claim 32 wherein said monomer comprises an ethylenically unsaturated compound.

37. The method of producing a porous chemically activated medium of claim 32 wherein said polymeric substrate and said chemically activated medium are microporous.

38. A porous biologically active medium having a low non-specific affinity for peptide group-containing materials comprising a porous polymeric medium having a low affinity for peptide group-containing materials, as measured by the Immersion Protein Binding Assay, and an acceptor molecule covalently bound to the porous polymeric medium through a residue of an activating agent.

39. The biologically active medium of claim 38 wherein said porous polymeric medium comprises a material rich in pendant hydroxyl groups.

40. The biologically active medium of claim 38 wherein the porous polymeric medium comprises
a porous polymeric substrate, and
a surface-modifying polymeric material having a low affinity for peptide group-containing materials formed at and covalently bonded to the surface of said porous polymeric substrate.

41. The biologically active medium of claim 39 wherein said acceptor molecule is bound to said covalently bound polymeric material.

42. The biologically active medium of claim 38 wherein said porous polymeric substrate comprises a polyamide.

43. The biologically active medium of claim 38 wherein said polyamide is nylon 66.

44. The biologically active medium of claim 40 wherein said biologically active medium is microporous and hydrophilic.

45. The biologically active medium of claim 40 wherein said acceptor molecule is a proteinaceous material.

46. The biologically active medium of claim 39 wherein said acceptor molecule comprises a biologically active material which is selected from the group consisting of a monoclonal antibody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, and a histone.

47. The biologically active medium of claim 39 wherein said peptide group-containing material comprises proteinaceous material and said porous polymeric medium has an adsorption of proteinaceous material measured by the Immersion Protein Binding Assay of not more than 30 micrograms per square centimeter.

48. The biologically active medium of claim 40 wherein said monomer from which said covalently bound surface-modifying polymeric material is formed is 2-hydroxyethyl acrylate, 2-hydroxyethyl methacrylate, hydroxypropyl acrylate, hydroxypropyl methacrylate and isomeric mixtures thereof.

49. The biologically active medium of claim 39 wherein said residue of an activating agent is a residue of a bisazolide.

50. The biologically active medium of claim 39 wherein said residue of an activating agent is a residue of a bisazolide of carbonic acid.

51. The biologically active medium of claim 39 wherein said residue of an activating agent is a residue of N,N'-carbonyldiimidazole.

52. The biologically active medium of claim 39 wherein the porous polymeric medium comprises
a porous polymeric substrate, and
a polymer coating having a low affinity for peptide group-containing materials formed at the surface of said porous polymeric substrate.

53. The biologically active medium of claim 52 wherein said biologically active material is bound to said porous polymeric substrate.

54. The biologically active medium of claim 52 wherein said porous polymeric substrate comprises a polyamide.

55. The biologically active medium of claim 52 wherein said polyamide is nylon 66.

56. The biologically active medium of claim 52 wherein said polymeric coating is formed from a polymer having a plurality of hydroxyl groups and a cross-linking agent having functional groups which react with the hydroxyl groups.

57. The biologically active medium of claim 52 wherein said biologically active medium is microporous and hydrophilic.

58. The biologically active medium of claim 56 wherein said hydroxyl group-containing polymer is hydroxypropyl cellulose.

59. The biologically active medium of claim 56 wherein said cross-linking agent is a copolymer of acrylic acid and N-methylol acrylamide.

60. The biologically active medium of claim 52 wherein said residue of an activating agent is a residue of a bisazolide.

61. The biologically active medium of claim 52 wherein said residue of an activating agent is a residue of a bisazolide of carbonic acid.

62. The biologically active medium of claim 52 wherein said residue of an activating agent is a residue of N,N'-carbonyldiimidazole.

63. The biologically active medium of claim 52 wherein said substrate comprises microporous, hydrophilic nylon 66, said polymer coating is a product formed from the reaction of hydroxypropyl cellulose and a copolymer of acrylic acid and N-methylol acrylamide and said activating agent is N,N'-carbonyldiimidazole.

64. The biologically active medium of claim 52 wherein said biologically active material is a proteinaceous material.

65. The biologically active medium of claim 52 wherein said biologically active material is selected from the group consisting of a monoclonal antiody, a polyclonal antibody, an antigenic substance, a glycoprotein, Protein A, a lectin, a carbohydrate, an enzyme substrate, a cofactor, an inhibitor, a hormone, an IgG class of immunoglobulin, a carrier protein, a receptor, heparin, a coagulation factor, and a histone.

* * * * *

UNITED STATES PATENT AND TRADEMARK OFFICE
CERTIFICATE OF CORRECTION

PATENT NO. : 4,886,836

DATED : December 12, 1989

INVENTOR(S) : Gsell et al

It is certified that error appears in the above-identified patent and that said Letters Patent is hereby corrected as shown below:

Column 23, line 34, after "material" insert --is formed--.

Column 24, line 14, before "the" (second occurrence) insert --wherein--.

Signed and Sealed this

First Day of June, 1993

Attest:

MICHAEL K. KIRK

*Attesting Officer*          Acting Commissioner of Patents and Trademarks